US005738728A

United States Patent [19]

Tisone

[11] Patent Number: 5,738,728
[45] Date of Patent: Apr. 14, 1998

[54] PRECISION METERED AEROSOL DISPENSING APPARATUS

[75] Inventor: Thomas C. Tisone, Orange, Calif.

[73] Assignee: Bio Dot, Inc., Irvine, Calif.

[21] Appl. No.: 687,711

[22] Filed: Jul. 26, 1996

[51] Int. Cl.$^6$ .......................... B05B 13/02; B05B 5/025
[52] U.S. Cl. .................... 118/638; 118/305; 239/346; 239/368; 239/369; 239/371
[58] Field of Search .......................... 118/683, 300, 118/305, 313; 239/346, 368, 369, 371

[56] References Cited

U.S. PATENT DOCUMENTS

| | | | |
|---|---|---|---|
| 2,264,564 | 12/1941 | Connor | 299/88 |
| 5,056,462 | 10/1991 | Perkins et al. | 118/683 |
| 5,183,742 | 2/1993 | Omoto et al. | |
| 5,366,158 | 11/1994 | Robisch et al. | 239/289 |
| 5,385,844 | 1/1995 | Kennamer et al. | 436/13 |
| 5,464,739 | 11/1995 | Johnson et al. | |
| 5,509,966 | 4/1996 | Sykes | 118/697 |

OTHER PUBLICATIONS

Bio-Dot, Inc. Product Catalog, (dates shown in paper 6).
IBC's 2nd Annual Conference on "MicroFabrication & Microfluidic Technologies, Advances in the Miniaturization of Bioanalytical Devices", Aug. 7 and 8, 1997, Renaissance Stanford Court Hotel, San Francisco, CA.
Series XY-3000 Brochure -Aug. 1994.
BioJet Specification -Sep. 1995.
Series MD-1000 Brochure -Aug. 1994.
BioDot AirJet-2000 Specification -Aug. 1994.
CV1000 Syringe Pump Dispenser -Aug. 1994.
BioDot, Inc. Brochure -Sep. 1995.

*Primary Examiner*—Donald E. Czaja
*Assistant Examiner*—Jacqueline A. Ruller
*Attorney, Agent, or Firm*—Knobbe, Martens, Olson & Bear, LLP

[57] ABSTRACT

A reagent dispensing apparatus is provided including a positive displacement syringe pump in series with an air brush dispenser. The pump is controlled by a stepper motor or the like to provide incremental or continuous flow of reagent to the air brush dispenser. The air brush dispenser mixes the predetermined incremental quantity or continuous flow of reagent with pressurized air to atomize the reagent and produce an aerosol spray pattern which coats the substrate.

30 Claims, 6 Drawing Sheets

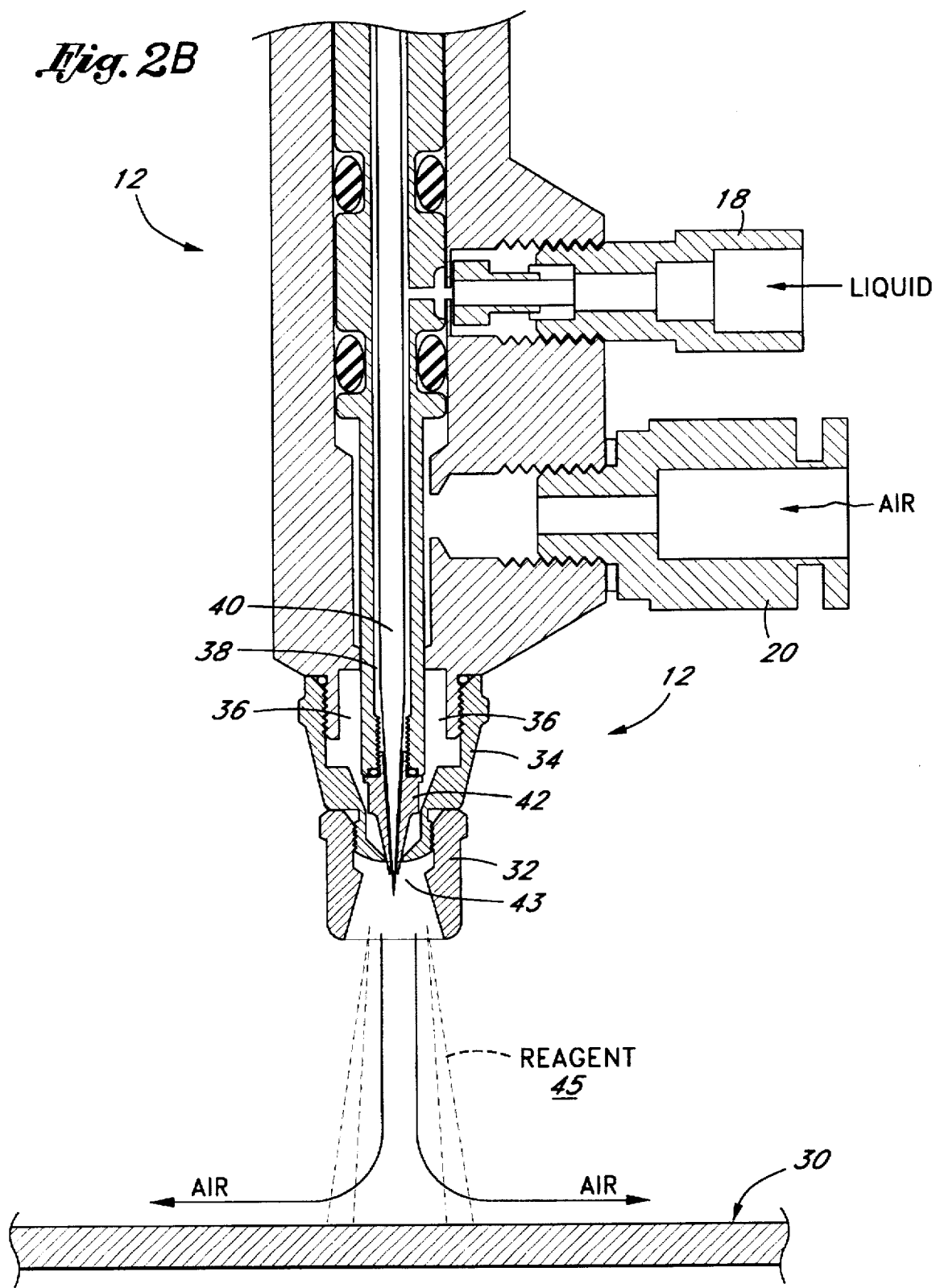

PRECISION METERED AEROSOL DISPENSING APPARATUS

BACKGROUND OF THE INVENTION

1. Field of the Invention

The present invention relates generally to an improved apparatus for coating chemical reagents onto a substrate and, in particular, to a precision metered aerosol dispensing system for coating precise quantities of chemical reagents onto a receptive membrane to form a diagnostic test strip.

2. Description of the Prior Art

Clinical testing of various bodily fluids conducted by medical personnel are well-established tools for medical diagnosis and treatment of various diseases and medical conditions. Such tests have become increasingly sophisticated, as medical advancements have led to many new ways of diagnosing and treating diseases.

The routine use of clinical testing for early screening and diagnosis of diseases or medical conditions has given rise to a heightened interest in simplified procedures for such clinical testing that do not require a high degree of skill or which a person may conduct on themselves for the purpose of acquiring information on a physiological relevant condition. Such tests may be carried out with or without consultation with a health care professional. Contemporary procedures of this type include blood glucose tests, ovulation tests, blood cholesterol tests and tests for the presence of human chorionic gonadotropin in urine, the basis of modern home pregnancy tests.

One of the most frequently used devices in clinical chemistry is the test strip or dip stick. These devices are characterized by their low cost and simplicity of use. Essentially, the test strip is placed in contact with a sample of the body fluid to be tested. Various reagents incorporated on the test strip react with one or more analytes present in the sample to provide a detectable signal.

Most test strips are chromogenic whereby a predetermined soluble constituent of the sample interacts with a particular reagent either to form a uniquely colored compound, as a qualitative indication of the presence or absence of the constituent, or to form a colored compound of variable color intensity, as a quantitative indication of the amount of the constituent present. These signals may be measured or detected either visually or via a specially calibrated machine.

For example, test strips for determining the presence or concentration of leukocyte cells, esterase or protease in a urine sample utilize chromogenetic esters which produce an alcohol product as a result of hydrolysis by esterase or protease. The intact chromogenetic ester has a color different from the alcohol hydrolysis product. The color change generated by hydrolysis of the chromogenetic ester, therefore provides a method of detecting the presence or concentration of esterase or protease, which in turn, is correlated to the presence or concentration of leukocyte cells. The degree and intensity of the color transition is proportional to the amount of leukocyte esterase or HLE detected in the urine. See U.S. Pat. No. 5,464,739.

The emergence and acceptance of such diagnostic test strips as a component of clinical testing and health care in general has led to the development of a number of quality diagnostic test strip products. Moreover, the range and availability of such products is likely to increase substantially in the future.

Because test strips are used to provide both quantitative and qualitative measurements, it is extremely important to provide uniformity in distribution of the reagents on the test strip substrate. The chemistry is often quite sensitive and medical practice requires that the testing system be extremely accurate. When automated systems are used, it is particularly important to ensure that the test strips are reliable and that the measurements taken are quantitatively accurate.

Application of one or more reagents to a test strip substrate is a highly difficult task. The viscosities and other flow properties of the reagents, their reactiveness with the substrate or other reagents vary from reagent to reagent, and even from lot to lot of the same reagent. It is also sometimes necessary or desirable to provide precise patterns of reagent on the test strip having predetermined reagent concentrations. For example, some test strips provide multiple test areas that are serially arranged so that multiple tests may be performed using a single test strip. U.S. Pat. No. 5,183,742, for instance, discloses a test strip having multiple side-by-side detection regions or zones for simultaneously performing various tests upon a sample of body fluid. Such test strip may be used to determine, for example, levels of glucose, protein, and the pH of a single blood sample. It is often difficult, however, to form sharp lines or other geometric shapes having uniform concentrations of reagent.

For several years the industry has been developing dispensing methods based on the use of air brushes. Air brushes use pressurized air flowing across a needle valve opening to atomize the reagent into a mist which is then deposited onto the test strip substrate. The quality of the mist, reagent dispersion pattern and the amount of reagent flow onto the substrate is controlled by adjusting the needle valve opening and/or the pressure of the atomizing air flow.

Current air brush dispensing techniques, however, are limited in the flexibility they have to independently adjust and regulate reagent dispersion, mist quality or size of droplets, and flow rates. Flow rates can often drift due to changes in temperature or the viscosity of the reagent. This can cause undesirable lot to lot variances of reagent coating concentrations. Many reagents that are used for diagnostic testing are so reactive with the receptive membrane or substrate that large droplets can form impressions on the membrane surface at the point of initial contact before the droplets flow together to form the desired pattern. Thus, it is sometimes desirable to dispense a fine mist of reagent containing very small droplets. Often, however, a desired mist quality or dispersion pattern is simply not attainable for a desired production flow rate. Thus, it is sometimes necessary to perform production runs of test strips at slower than optimal speeds in order to ensure adequate dispersion and atomization of reagent and uniformity of substrate coating. This can increases the cost of production significantly.

While some of these problems can be controlled or mitigated by adding surfactants or various other chemical additives to modify the surface tension or other flow characteristics of the droplets, compatible chemistry is not available for all reagents. Also the use of surfactants and other chemicals can often lead to other problems either in the test strip itself or in the dispensing apparatus or production process.

SUMMARY OF THE INVENTION

The reagent dispensing apparatus of the invention can uniformly dispense chemical reagents onto a receptive membrane while providing the ability to independently, cost effectively, and precisely adjust reagent dispersion patterns, mist quality, or droplet size and production flow rates.

In accordance with one preferred embodiment, the present invention comprises a reagent dispensing apparatus including a positive displacement syringe pump provided in series with an air brush dispenser. The pump is controlled by a stepper motor or the like to provide precision incremental or continuous flow of reagent to the air brush dispenser. The air brush dispenser mixes the incremental quantity or continuous flow of reagent with pressurized air to atomize the reagent and produce an aerosol mist of a given dispersion pattern which then coats the substrate. Advantageously, the mist quality, flow rate and dispersion pattern of the reagent can be precisely controlled independently of the particular operating parameters of the air brush dispenser. Thus, new spray patterns having improved atomization of reagent and dispensing performance can be achieved.

In accordance with another preferred embodiment, the present invention comprises a reagent dispensing apparatus including a platform for supporting a test strip substrate or membrane and a carriage supported on the platform and adapted for X, X-Y or X-Y-Z motion relative thereto. An air brush dispenser is mounted on the carriage such that it can dispense reagent in a controlled and exacting manner on the reagent test strip to form lines, spots or other geometric patterns, as desired. A positive displacement syringe pump is provided in series with the air brush dispenser and is controlled by a stepper motor or the like to provide incremental or continuous flow of reagent to the air brush dispenser. The air brush mixes the incremental quantity for continuous flow of reagent with pressurized air to atomize the reagent and produce and aerosol mist with a given dispersion pattern which then coats the substrate. The positive displacement syringe pump is preferably electronically controlled and may be coordinated with X, X-Y or X-Y-Z motion of the carriage so that reagent density may be input in terms of flow or volume per unit length. As a result, the present invention allows the desired input flow rate parameter to directly dictate the performance of the dispenser, rather than being determined by system parameters such as input air pressure, orifice settings and the particular viscosity and other flow characteristics of the reagent.

These and other objects and advantages of the present invention will be readily ascertainable from the following detailed description of the preferred embodiments, having reference to the attached drawings, the invention not being limited to any particular preferred embodiment.

BRIEF DESCRIPTION OF THE FIGURES

FIGS. 2A and 2B are a cross-sectional and detail views, respectively, of the air brush dispenser of FIG. 1;

DETAILED DESCRIPTION OF THE PREFERRED EMBODIMENTS

Figure 1:
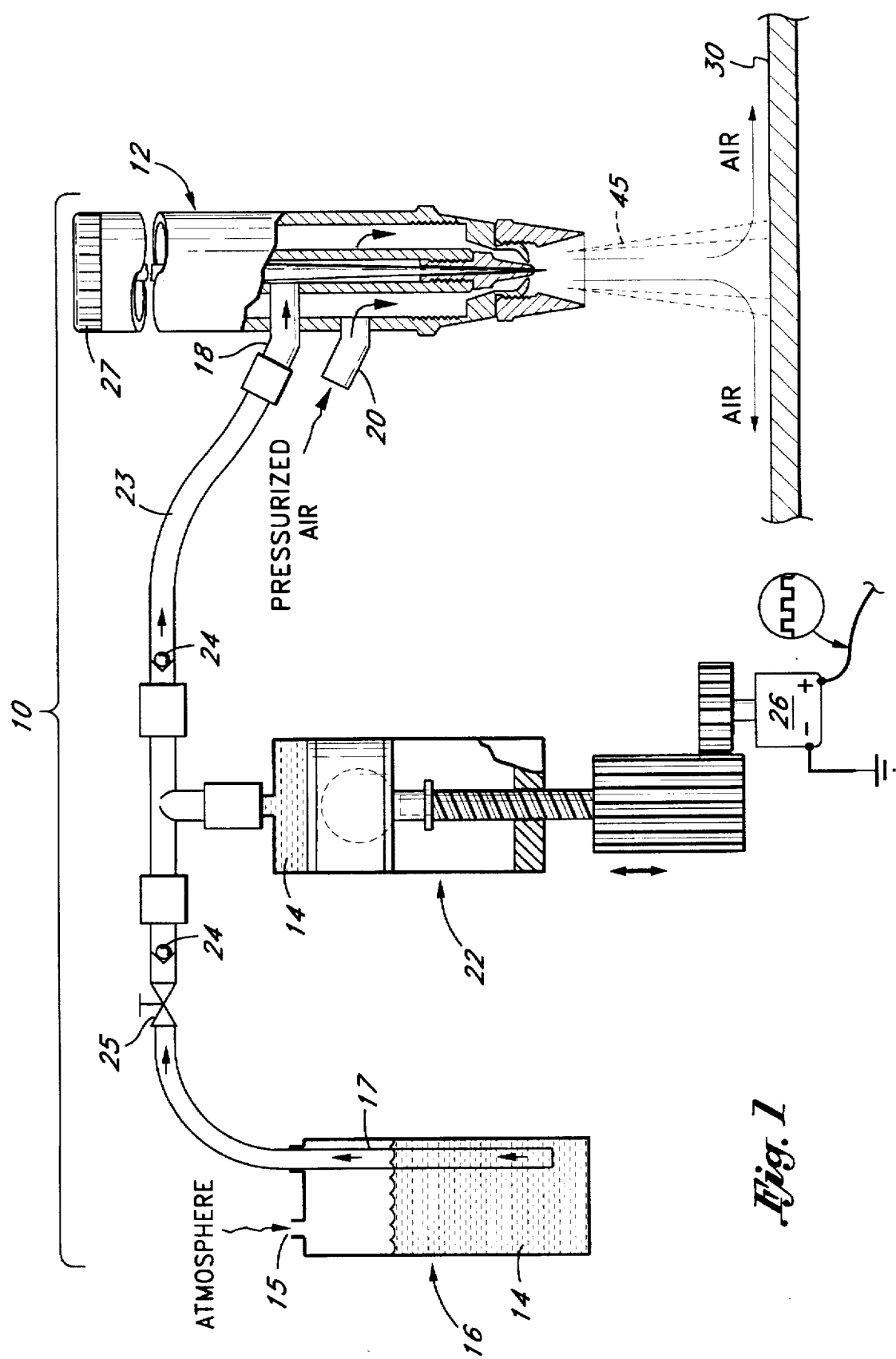
FIG. 1 is a schematic drawing of a precision metered aerosol dispensing apparatus having features in accordance with the present invention.

FIG. 1 shows a precision metered aerosol dispensing apparatus 10 having features in accordance with the present invention. The dispensing apparatus 10 generally comprises a conventional airbrush dispenser connected in series with a positive displacement syringe pump 22 for dispensing reagent 14 from a reservoir 16. The air brush 12 has two inlet ports 18, 20. One port 20 is connected to a source of pressurized air. The other port 18 is connected to a source of reagent, in this case the positive displacement pump 22.

Air Brush Dispenser

Figure 2A:
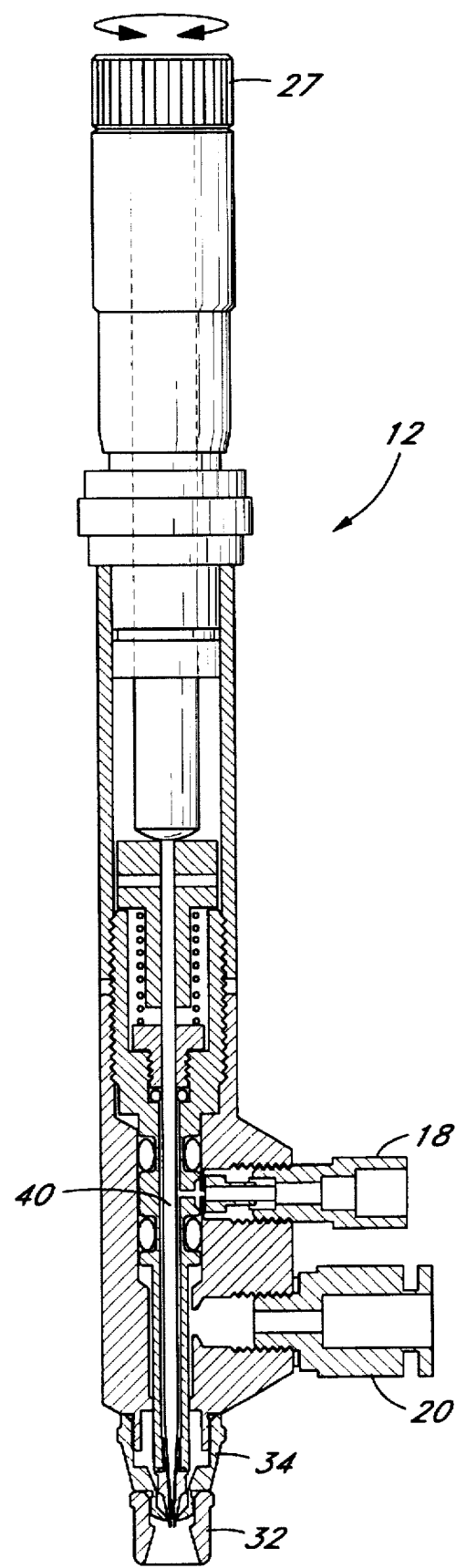

FIGS. 2A and 2B are cross-sectional and detail views, respectfully, of the air brush dispenser 12, shown in FIG. 1. The dispenser 12 generally comprises a nozzle portion 32 and a manifold portion 34. The manifold 34 allows compressed air to enter into a first annular chamber 36 and allows reagent to enter into a second annular chamber 38 formed between a needle valve 40 and a corresponding orifice 42. The needle valve 40 is fitted within and extends through the orifice 42, as shown. It is preferably axially adjustable in accordance with well-known needle valve adjustment techniques. The position of the needle valve 40 relative to the orifice 42 determines the effective size of the resulting needle valve opening 43, and thus the amount of reagent flow for a given pressure differential.

Pressurized air flows over the needle valve opening 43 creating a venturi effect which draws reagent through the orifice 42 onto the tip of the needle valve 40. The pressurized air accelerates past the orifice 42 and the needle valve opening 43 over the tip of the needle 40. The resulting high velocity air atomizes the reagent 14 flowing down the needle 40. This creates an aerosol mist 45 which is ejected from the nozzle 32 along with the excess airflow. In a conventional air brush dispenser, the volume of reagent dispensed by the nozzle 32 is determined by the pressure differential of the compressed air source relative to atmospheric pressure, the size of the needle valve opening 43, and the viscosity and other flow characteristics of the reagent 14.

In accordance with the present invention, however, a positive displacement pump 22 is placed in series between the reservoir 16 and the air brush 12 as shown in FIG. 1. The orifice 42 now admits a flow of reagent as determined solely by the positive displacement pump 22. The reagent is ejected out of the orifice opening 42 and mixes with the pressurized air flowing out of the nozzle 32. Advantageously, in accordance with the present invention absolute volume or flow rate is an input parameter controlled by the metering pump, rather than an output parameter which must be calibrated by trial and error adjustment. Thus, the air brush can be used to deliver precise quantities and flow rates of reagent onto a test strip substrate. This substrate is prefferably a receptive membrane adapted to bond with the reagent so as to form a diagnostic test strip. However, the substrate 30 may also be paper, celluous, plastic or any wet or dry surface capable of receiving a dispensed reagent or other liquid.

As discussed in more detail below, the combination of an air brush dispenser and a metering pump provides a new dimension of control which provides additional production capabilities not achievable with conventional air brush dispensers. Unlike conventional air brush dispensers, which typically have only a single stable operating point for a given input air pressure and needle valve opening, the present invention provides a wide range of metered flow rates for achieving a stable dispersion pattern. The limits of this range can be determined experimentally. An even wider range of production flow rates can be achieved using a single pressure setting and a series of adjustable orifice openings. A useful product can be configured, for example, using an air brush dispenser with either a fixed, click-stop or continuous orifice setting mechanism.

Figure 3:
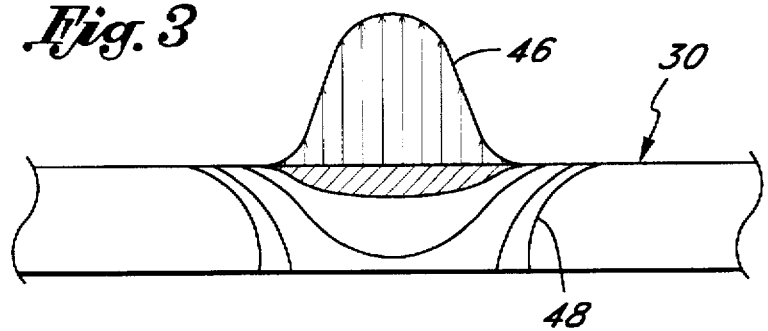
FIG. 3 is a graphical representation of the test strip substrate of FIG. 2, illustrating surface concentration of dispensed reagent and the resulting concentration gradients of the absorbed reagent.

FIG. 3 is a graphical representation of the test strip membrane 30 of FIG. 2B, illustrating surface concentration 46 of dispensed reagent and the resulting concentration gradients 48 of the absorbed reagent in the membrane 30. For stable dispersion patterns, the surface reagent concentration 46 assumes a standard Gausian distribution, as shown. The width or standard deviation of the distribution pattern will depend upon the shape of the dispersion pattern created by the nozzle 32 (FIG. 2B). This is dependant primarily on the shape of the exit nozzle 32, the needle valve 40 and the input air pressure. Higher input pressures will generally result in wider dispersion patterns.

Syringe Pump

Figure 4:
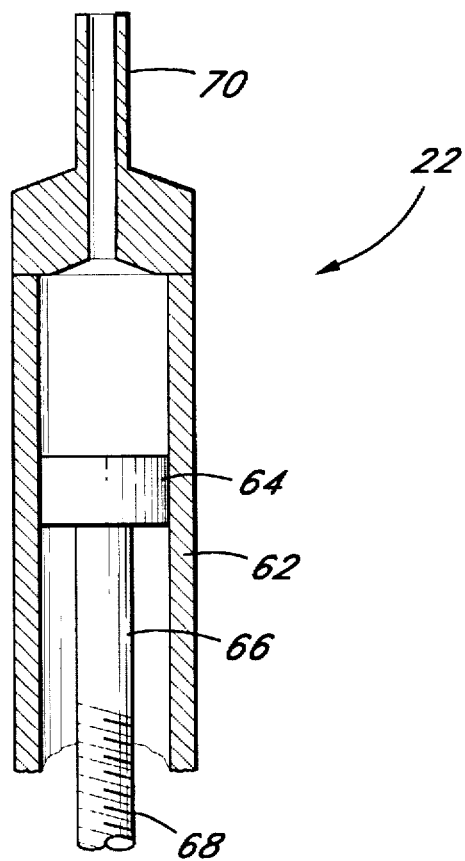
FIG. 4 is a cross-sectional detail view of the syringe pump of FIG. 1.

The positive displacement pump 22 may be any one of several varieties of commercially available pumping devices for metering precise quantities of liquid. A syringe-type pump 22, as shown in FIG. 1, is preferred because of its convenience and commercial availability. A wide variety of other pumps may used, however, to achieve the benefits and advantages as disclosed herein. These may include, without limitation, rotary pumps, peristaltic pumps, squash-plate pumps, and the like. As illustrated in more detail in FIG. 4, the syringe pump 22 generally comprises a syringe housing 62 of a predetermined volume and a plunger 64 which is sealed against the syringe housing by O-rings or the like. The plunger 64 mechanically engages a plunger shaft 66 having a lead screw portion 68 adapted to thread in and out of a base support (not shown). Those skilled in the art will readily appreciate that as the lead screw portion 68 of the plunger shaft 66 is rotated the plunger 64 will be displaced axially, forcing reagent from the syringe housing 62 into the exit tube 70. Any number of suitable motors or mechanical actuators may be used to drive the lead screw 68. Preferably, a stepper motor 26 (FIG. 1) or other incremental or continuous actuator device is used so that the amount and/or flow rate of reagent can be precisely regulated.

Suitable syringe pumps are commercially available, such as the Bio-Dot CV1000 Syringe Pump Dispenser, available from Bio-Dot, Inc. of Irvine, Calif. This particular syringe pump incorporates an electronically controlled stepper motor for providing precision liquid handling using a variety of syringe sizes. The CV1000 is powered by a single 24 DC volt power supply and is controlled via an industry-standard RS232 or RS485 bus interface. The syringe pump may have anywhere from 3,000–24,000 steps, although higher resolution pumps having 48,000 steps or more may also be used to enjoy the benefits of the invention herein disclosed. Higher resolution pumps, such as piezoelectric pumps, may also be used to provide even finer resolutions as desired. The lead screw 68 may optionally be fitted with an optical encoder or similar device to detect any lost steps. Alternatively, the lead screw of the metering pump can be replaced with a piezoelectric slide to provide both smaller volume increments and also faster acceleration/deceleration characteristics. Multiple syringe pumps may also be used in parallel, for example, for delivering varying concentrations of reagent and/or other liquids to the dispenser or for alternating dispensing operations between two or more reagents.

The travel of the plunger 64 is preferably about 60 mm. Plunger speeds may range from 0.8 seconds per stroke with a 10-step minimum for low-resolution pumping or 1.5 seconds per stroke with a 20-step minimum for high-speed resolution pumping. The stroke speed may vary depending upon the syringe size and the tubing used. Syringes may vary from less than 50 microliters to 25 milliliters, or more as needed. For most reagent dispensing applications it should be adequate to provide a syringe having a volume from about 500 microliters to about 25 milliliters. The minimum incremental displacement volume of the pump will depend on the pump resolution and syringe volume. For example, for a syringe housing volume of 500 microliters and 12,000 step resolution pump the minimum incremental displacement volume will be about 4.2 nanoliters. Minimum incremental displacement volumes from about 2.1 nanoliters to 2.1 microliters are preferred, although higher or lower incremental displacement volumes may also be used while still enjoying the benefits of the present invention.

The syringe housing 62 may be made from any one of a number of suitable bio compatible materials such as glass, Teflon™ or Kel-F. The plunger 64 is preferably formed of virgin Teflon™. As shown in FIG. 1, the syringe is connected to the air brush dispenser using a Teflon tubing 23, such as ¼-inch O.D. tubing provided with luer-type fittings for connection to the syringe and inlet port of the air brush dispenser. Various check valves 24 or shut-off valves 25 may also be used, as desired, to direct the flow of reagent to and from the reservoir 16, syringe pump 22 and dispenser 12.

Reagent Reservoir

The reagent reservoir 16 may be any one of a number of suitable receptacles capable of allowing a liquid reagent 14 to be siphoned into pump 22. The reservoir may be pressurized, as desired, but is preferable vented to the atmosphere, as shown, via a vent opening 15. The particular size and shape of the reservoir 16 is relatively unimportant.

A siphon tube 17 extends downward into the reservoir 16 to a desired depth sufficient to allow siphoning of reagent 14. Preferably the siphon tube 17 extends as deep as possible into the reservoir 16 without causing blockage of the lower inlet portion of the tube 17. Optionally, the lower inlet portion of the tube 17 may be cut at an angle or have other features as necessary to desirable to provide consistent and reliable siphoning of reagent 14.

Operation

A key operational advantage achieved by the present invention is that over a given range the flow of reagent is substantially independent of the input air pressure and needle valve opening of the air brush and the particular flow characteristics of the reagent. This is because the quantity of reagent dispensed is precisely controlled by the positive displacement pump 22. This has particular advantage, for example, in applications requiring a very fine mist of reagent or for higher viscosity reagents, since the reagent flow can be precisely controlled without substantial regard to the flow parameters otherwise required to achieve a stable dispersion pattern.

For example, with a conventional air brush dispenser in order to obtain a very fine mist, one must attempt to close down the needle valve opening to make it as small as possible, while at the same time increasing the pressure of the air flow to provide significant venturi effect. However, as the needle valve opening becomes more and more restricted, surface adhesion and capillary effects begin to counterbalance the venturi effect pressure, and, thus, prevent or restrict flow through extremely small orifice openings. Even if stable flow could be achieved by increasing the inlet air pressure, the pressure increase could undesirably affect the shape or dispersion pattern of the flow.

Figure 5:
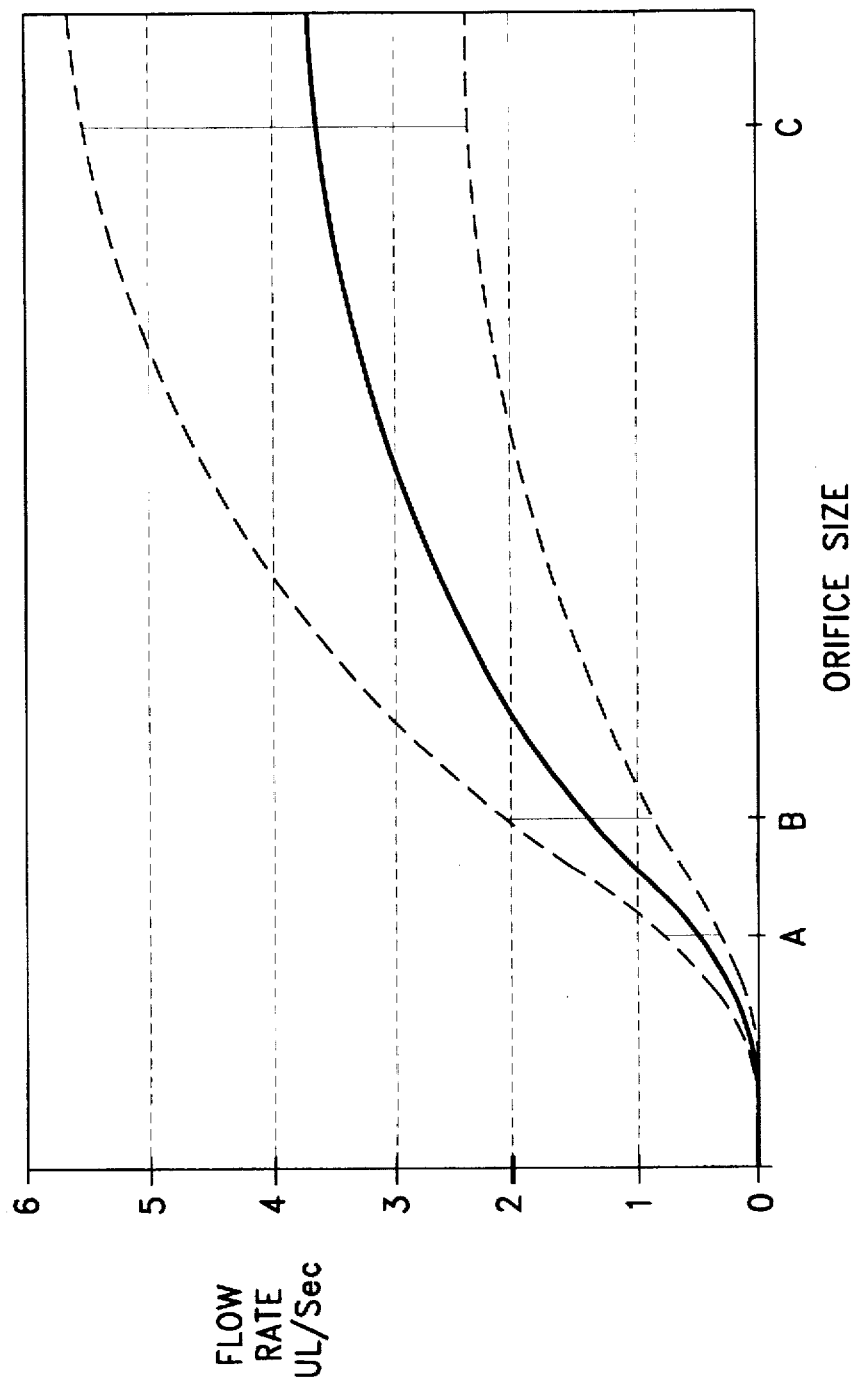
FIG. 5 is a graph comparatively illustrating the range of flow rates attainable with a precision metered aerosol dispensing apparatus constructed in accordance with the present invention.

The present invention, however, overcomes these and other problems of the prior art by precisely metering the reagent so that capillary action and other flow effects do not significantly affect the operation of the dispenser such that the amount of reagent can be precisely regulated over a wide range. This feature enables reagent dispersion patterns, mist quality or droplet size, and flow rates to be varied dramatically from one range to another. Much finer mists can also be achieved than with conventional air brush dispensers. Thus, the present invention not only provides precise metering of reagent, but also adds a new dimension of operation of the air brush dispenser not before possible. FIG. 5 comparatively illustrates the range of flow rates and operating conditions for given orifice openings attainable with an aerosol dispensing apparatus constructed in accordance with the present invention versus a conventional aerosol dispenser.

The present invention has particular advantage for high production processing of test strips. In certain production applications, for example, it may be desirable to provide a very fine mist of reagent with a given dispersion to provide optimal coating characteristics. At the same time, it is desirable to provide high reagent flow rates for increased production levels. Typically, with a conventional air brush dispenser, as one increases the output flow rate, the size of the orifice must be opened. But the larger the orifice is, the larger the drop size of the particles or droplets will be. The present invention allows the use of a smaller orifice opening to attain high flow rates by positively displacing the reagent through the smaller orifice opening. In other words, the flow of reagent is not substantially dependent on the orifice size. It is dependent only on the displacement of the syringe pump which acts as the forcing function for the entire system.

Of course, there will be a maximum range of operation for each orifice opening. The higher limit will be the maximum amount of reagent that can be forced through the orifice at maximum design pressure. The lower limit will be determined by the stability of the resulting aerosol spray pattern. If the orifice is too small for a given flow rate, the pressures in the dispenser will become too great, causing possible rupture or other damage to the system. If the orifice opening is too large for a given flow rate, the spray will tend to pulsate or spatter as localized turbulence and surface adhesion effects cause large fluctuations in the amount of reagent dispensed from the orifice opening. The orifice size is preferably adjusted (via the needle valve) to provide a stable dispersion pattern of reagent. This range can be determined experimentally for a given production setup.

Dispensing Platforms

In a particularly preferred mode of operation, the dispensing apparatus may be integrated to an X, X-Y, or X-Y-Z carriage/platform wherein the programmed motion control can be coordinated with the metering pump to deliver a desired volume per unit length, with the ability to also independently control the dispersion pattern and mist quality of the reagent being delivered. For example, it is possible to deliver reagent at a rate of 1 microliter per centimeter at a constant table speed with a given spray dispersement pattern and mist quality. The timing and coordination of the air brush dispenser relative to the syringe pump and movable carriage/platform can be accomplished using any one of a number controllers well known in the art. Typical controllers are microprocessor based and provide any one of a number of output control pulses or electrical signals of predetermined phase, pulse width and/or frequency. These signals may be used, for example, to control and coordinate the syringe pump, movable carriage/platform and air brush dispenser in accordance with the present invention. In this context, there are basically two desirable modes of dispensing operation: (1) line or continuous dispensing; and (2) spot dispensing. In the case of continuous dispersing, the pump 22 is set to a predetermined flow rate to deliver a metered volume of reagent per unit time. For example, the flow rate could be programmed to deliver 1 microliter per second. The syringe pump 22 will then deliver reagent 14 to the air brush dispenser 12 at the predetermined rate. The air brush dispenser will mix the reagent with air, forming a mist that is deposited on the test strip. Thus, in the continuous operation mode, the system is not only capable of delivering precise metered flow rates of reagent, but this can be done with independent control of table speed, reagent concentration per unit length, and mist quality. If desired, a continuous drive reagent pump may be used to assure a steady flow rate of reagent to the air brush, rather than a pulsed flow.

A second mode of operation involves dispensing "spot" spray patterns at pre-programmed positions. This may be done, for example, by synchronizing the displacement pump and air brush dispenser with a programmable X-Y table. A dispensing apparatus in accordance with the present invention will provide a spot size determined by the metering pump increment, i.e., a 50-microliter syringe with 12,000 steps will provide an incremental displacement volume of 4.16 nanoliters.

Figure 6:
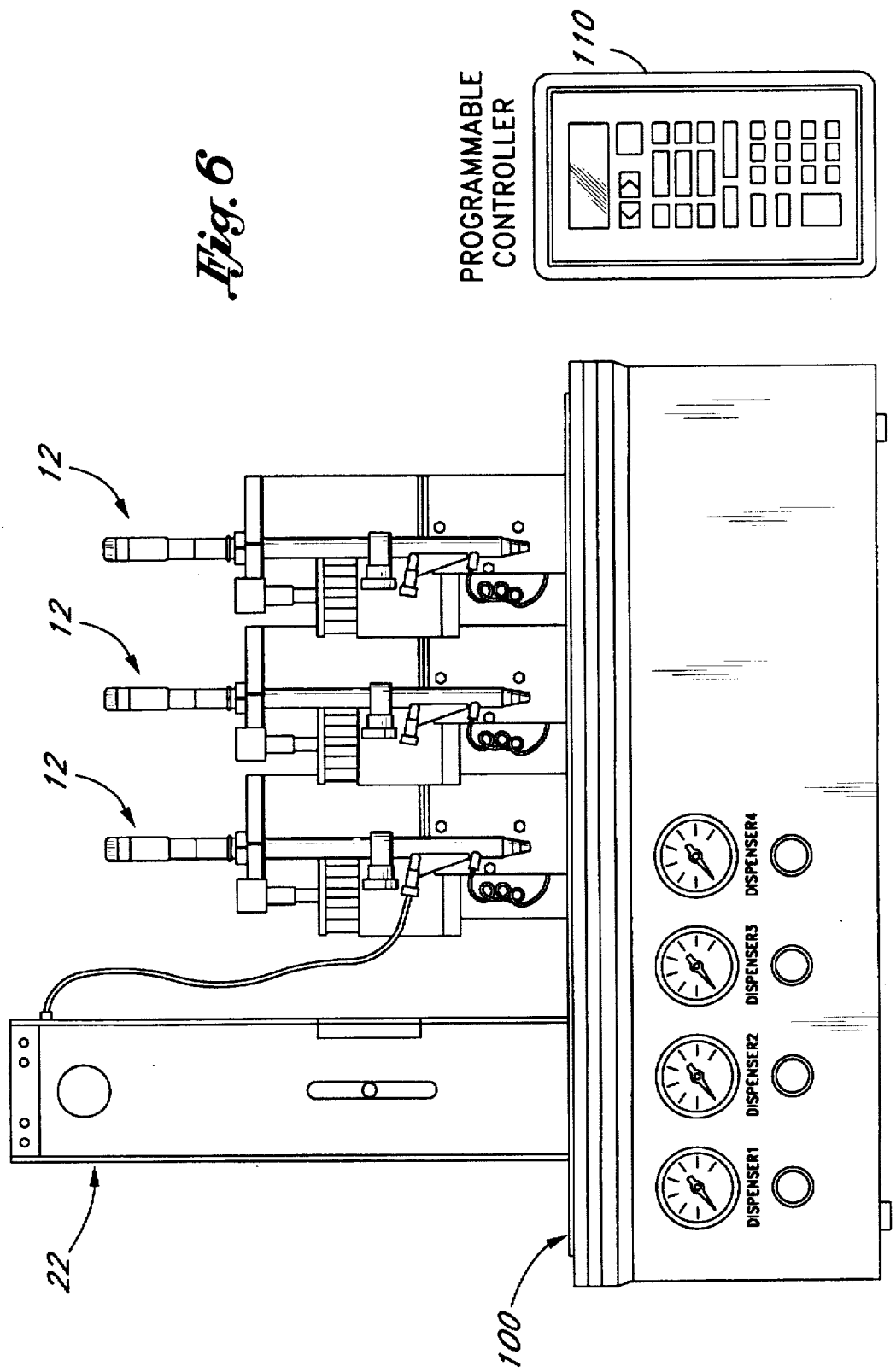
FIG. 6 is an elevational view of an optional dispensing platform for use in accordance with the present invention.

The dispensing apparatus in accordance with the present invention may also be mounted on any one of a number of membrane placement and handling modules. For instance, a single platform 100 may be used to mount multiple dispensers to handle one or more reagents, as shown in FIG. 6. Such dispensing platforms 100 may be microprocessor-based and are preferably controlled through an industry standard input/output I-O system, such as an RS232 interface. A remote programmer 110 may also be used, as desired. The invention is also well suited for use with individual membrane strip handling modules and continuous reel-m-reel handling modules (not shown). An individual membrane strip module may incorporate an X-Y table motion for dispensing. The reel-to-reel platform may incorporate constant-speed membrane transport with mountings attached for motion of one or more dispensers. A drying oven (not shown) may also be used to increase production throughput, as desired.

The dispensing apparatus of the present invention can be used to dispense a wide variety of liquids, reagents and other substances. Although the invention has been disclosed in the context of certain preferred embodiments, it will be understood that those skilled in the art that the present invention extends beyond the specifically disclosed embodiments to other alternative embodiments of the invention. Thus, it is intended that the scope of the invention should not be limited by the particularly disclosed embodiment described above, but should be determined only by reference to the claims that follow.

What is claimed is:

1. An apparatus for dispensing a liquid, comprising:
    an aerosol dispenser having an air inlet port and a liquid inlet port for mixing said liquid with a predetermined flow of said air to form an aerosol mist; and
    a positive displacement pump in fluid communication with the liquid inlet port of said aerosol dispenser for metering predetermined quantities of said liquid to said liquid inlet port of said aerosol dispenser;
    whereby the quantity and/or flow rate of liquid dispensed by said aerosol dispenser can be precisely metered substantially without being affected by the particular operating parameters of said aerosol dispenser or the particular flow characteristics of said liquid being dispensed.

2. The dispensing apparatus of claim 1 wherein said liquid comprises a chemical reagent.

3. The dispensing apparatus of claim 1 wherein said aerosol dispenser comprises an air brush dispenser.

4. The dispensing apparatus of claim 3 wherein said aerosol dispenser comprises an adjustable needle valve that opens and closes an orifice through which said liquid flows.

5. The dispensing apparatus of claim 1 wherein said positive displacement pump comprises a syringe pump.

6. The dispensing apparatus of claim 5 wherein said syringe pump comprises a syringe housing, a plunger axially displaceable within said syringe housing and plunger shaft having a lead screw formed thereon.

7. The dispensing apparatus of claim 6 wherein said lead screw is sized and positioned such that when said lead screw is rotated, said plunger is displaced axially, causing a predetermined quantity of said liquid to be delivered to said liquid inlet port of said aerosol dispenser.

8. The dispensing apparatus of claim 6 wherein said housing has a volume of between about 25 microliters about 25 milliliters.

9. The dispensing apparatus of claim 1 further comprising a stepper motor adapted to cause said pump to dispense predetermined incremental quantities of said liquid to said aerosol dispenser.

10. The dispensing apparatus of claim 9 wherein said positive displacement pump has an incremental displacement volume of between about 0.42 nanoliters and 2.1 microliters.

11. The dispensing apparatus of claim 9 wherein said positive displacement pump has an incremental displacement volume of less than about 4.2 nanoliters.

12. The dispensing apparatus of claim 1 wherein said positive displacement pump has a resolution of between about 3,000 and 48,000 steps.

13. The dispensing apparatus of claim 10 wherein said positive displacement pump has a resolution of at least about 12,000 steps.

14. An apparatus for dispensing a liquid reagent onto a substrate, comprising:
   an air brush dispenser having an air passage terminating in a nozzle and a liquid reagent passage terminating in a mixing chamber for mixing said liquid reagent with a flow of said air to form an aerosol mist proximate said substrate; and
   a positive displacement syringe pump in fluid communication with said liquid reagent passage for metering predetermined quantities of said liquid reagent to said air brush dispenser;
   whereby the quantity and/or flow rate of said liquid dispensed by said air brush dispenser can be precisely metered substantially without regard to the particular operating conditions of said air brush.

15. The dispensing apparatus of claim 14 wherein said air brush dispenser comprises an adjustable needle valve adapted to adjust the size of an orifice.

16. The dispensing apparatus of claim 14 wherein said syringe pump comprises a syringe housing, a plunger axially displaceable within said syringe housing and a plunger shaft having a lead screw formed thereon.

17. The dispensing apparatus of claim 16 wherein said lead screw is sized and positioned such that when said lead screw is rotated, said plunger is displaced axially, causing a predetermined quantity of said liquid to be delivered to said liquid inlet port of said air brush dispenser.

18. The dispensing apparatus of claim 14 wherein said positive displacement syringe pump comprises a stepper motor adapted to cause said pump to dispense incremental quantities of said liquid to said air brush dispenser.

19. The dispensing apparatus of claim 18 wherein said positive displacement syringe pump has an incremental displacement volume of less than about 4.2 nanoliters.

20. The dispensing apparatus of claim 1 in combination with a platform for supporting a substrate and a carriage mounted on said platform and being adapted for X, X-Y or X-Y-Z motion relative to said platform and wherein said aerosol dispenser is mounted in juxtaposition with said carriage and/or said platform.

21. The dispensing apparatus of claim 20 further comprising a controller in communication with said positive displacement pump and said carriage for coordinating the output of said pump with the relative movement of said carriage so that said liquid may be dispensed in precise quantities of flow per unit length of said substrate.

22. The dispensing apparatus of claim 14 in combination with a platform for supporting said substrate and a carriage mounted on said platform and being adapted for X, X-Y or X-Y-Z motion relative to said platform and wherein said air brush dispenser is mounted in juxtaposition with said carriage and/or said platform.

23. The dispensing apparatus of claim 20 further comprising a controller in communication with said positive displacement syringe pump and said carriage for coordinating the output of said pump with the relative movement of said carriage so that said liquid may be dispensed in precise quantities of flow per unit length of said substrate.

24. An apparatus for forming a diagnostic test strip comprising:
   a support carriage and/or platform for movably transporting a receptive substrate;
   a pump for metering a predetermined quantity or flow rate of liquid reagent to be dispensed;
   an aerosol dispenser for receiving said metered quantity or flow rate of liquid reagent and mixing it with air to form an aerosol mist which is deposited on said receptive substrate; and
   means for regulating the metering of said predetermined quantity or flow rate of liquid reagent and the transporting of said receptive substrate such that the dispensing of said reagent may be controlled in terms of volume of reagent per unit length of substrate substantially independently of the particular operating characteristics of said aerosol dispenser and the flow characteristics of said liquid reagent being dispensed.

25. The apparatus of claim 24 wherein said aerosol dispenser comprises an air brush dispenser.

26. The apparatus of claim 24 wherein said aerosol dispenser comprises an adjustable needle valve that adjusts the size of an orifice through which said liquid flows.

27. The apparatus of claim 24 wherein said pump comprises a positive displacement pump.

28. The apparatus of claim 27 wherein said positive displacement pump comprises a syringe pump.

29. The apparatus of claim 24 further comprising a stepper motor adapted to cause said pump to dispense predetermined incremental quantities of said liquid to said aerosol dispenser.

30. The apparatus of claim 24 wherein said regulating means comprises a controller in communication with said pump and said carriage for coordinating the output of said pump with the relative movement of said carriage so that said liquid reagent may be dispensed in quantities of volume per unit length of said substrate.

* * * * *

UNITED STATES PATENT AND TRADEMARK OFFICE
CERTIFICATE OF CORRECTION

| | | |
|---|---|---|
| PATENT NO. | : 5,738,728 | Page 1 of 1 |
| APPLICATION NO. | : 08/687711 | |
| DATED | : April 14, 1998 | |
| INVENTOR(S) | : Thomas C. Tisone | |

It is certified that error appears in the above-identified patent and that said Letters Patent is hereby corrected as shown below:

At Column 10, line 23 in Claim 23, after "displacement" please delete "syringe".

Signed and Sealed this
Nineteenth Day of June, 2012

David J. Kappos
*Director of the United States Patent and Trademark Office*